(12) United States Patent
Almaguer

(10) Patent No.: US 6,768,299 B2
(45) Date of Patent: Jul. 27, 2004

(54) DOWNHOLE MAGNETIC-FIELD BASED FEATURE DETECTOR

(75) Inventor: James S. Almaguer, Richmond, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 10/028,835

(22) Filed: Dec. 20, 2001

(65) Prior Publication Data
US 2003/0117134 A1 Jun. 26, 2003

(51) Int. Cl.[7] ............................................. G01N 27/72
(52) U.S. Cl. ...................................... 324/221; 324/220
(58) Field of Search ................................. 324/219, 220, 324/221, 238, 239, 240, 241, 242, 243

(56) References Cited

U.S. PATENT DOCUMENTS

| | | | |
|---|---|---|---|
| 2,250,703 A | 7/1941 | Crites et al. | |
| 2,967,994 A | 1/1961 | Peterson | |
| 3,015,063 A | * 12/1961 | Ownby | ........................ 324/221 |
| 3,114,876 A | * 12/1963 | Schuster | ..................... 324/221 |
| 3,126,058 A | 3/1964 | Yetman et al. | |
| 3,434,046 A | 3/1969 | Wilson et al. | |
| 4,292,589 A | 9/1981 | Bonner | |
| 4,323,848 A | 4/1982 | Kuckes | |
| 4,349,781 A | 9/1982 | Vozoff | |
| 4,437,064 A | 3/1984 | Overton, Jr. et al. | |
| 4,443,762 A | 4/1984 | Kuckes | |
| 4,529,939 A | 7/1985 | Kuckes | |
| 4,625,795 A | 12/1986 | Despax et al. | |
| 4,792,761 A | * 12/1988 | King et al. | ................. 324/345 |
| 4,800,753 A | 1/1989 | Despax et al. | |
| 4,808,925 A | 2/1989 | Baird | |
| 5,061,896 A | 10/1991 | Schmidt | |
| 5,130,653 A | 7/1992 | Wu et al. | |
| 5,475,310 A | 12/1995 | Pocachard et al. | |
| 5,530,349 A | 6/1996 | Lopez et al. | |
| 5,668,475 A | 9/1997 | Orban et al. | |
| 5,720,345 A | * 2/1998 | Price et al. | .............. 166/254.2 |
| 5,905,379 A | 5/1999 | Orban et al. | |
| 6,411,084 B1 | * 6/2002 | Yoo | ........................... 324/221 |
| 6,518,754 B1 | * 2/2003 | Edwards | ..................... 324/300 |

* cited by examiner

Primary Examiner—Jay Patidar
(74) Attorney, Agent, or Firm—Trop, Pruner & Hu P.C.; Jeffrey Griffin; Brigitte Jeffery Echols

(57) ABSTRACT

An apparatus that is usable with a subterranean well includes a magnetometer and a circuit. The magnetometer indicates a strength of a magnetic field that at least partially extends through a portion of a downhole pipe. The circuit is coupled to the magnetometer to indicate a feature present in the pipe based on the indication from the magnetometer.

35 Claims, 3 Drawing Sheets

DOWNHOLE MAGNETIC-FIELD BASED FEATURE DETECTOR

BACKGROUND

The invention generally relates to a downhole magnetic-field based feature detector for detecting features of a downhole pipe.

Certain downhole oilfield applications, such as perforating applications, require the ability to be able to position a tool at a particular and known spot in the well. For example, a wireline (armored electric cable) service uses a tool assembly (e.g., instrument) that is lowered downhole via a wireline. A depth counter may be used at surface to track the length of the dispensed cable to approximate the depth of the tool assembly. However, because the depth counter does not precisely indicate the depth (primarily because of stretch in the cable), other techniques may be used.

For example, a more precise technique may use a depth control or depth correlation log (e.g., casing collar locator log), a log that is run while ascending & descending in the well indicates the depths of various casing collar joints of the well. In this manner, the well includes casing collar joints, joints at which casing segments are coupled together to form the well casing. Each casing collar joint includes a casing collar to couple two adjacent casing segments of the well casing together. An air gap may exist between the ends of adjacent casing segments.

To obtain the depth control log, a wireline tool assembly may be run downhole and include a detection device, called a casing collar locator, to detect the casing collar joints. When the casing collar locator indicates detection of a casing collar joint, the coarse depth that is provided by the depth counter may be used to locate the corresponding casing collar joint on the depth control log. Because the depth control log precisely shows the depth of the detected casing collar joint, the precise depth of the tool assembly may be determined. From this determination, an error compensation factor may be derived. Then, when a perforating gun is positioned downhole, the error compensation factor is used to compensate the reading of the depth counter to precisely position the gun.

A conventional casing collar locator is a passive device that uses the principle of magnetic inductance to detect casing collar joints. In this manner, the casing collar locator typically includes an electrical coil, or winding, through which a magnetic flux field that is created by one or more permanent magnets passes. When a change occurs in the effective magnetic permeability in the surrounding, such as in the presence of a casing collar joint, a voltage is induced on the coil winding due to the corresponding change in the magnetic flux field (disturbance). Therefore, as the casing collar locator passes the casing collar joint, the change in permeability (caused by such things as the presence of the air gap between adjacent well casing segments and the casing collar) causes a change in the magnetic flux field to induce a signal across the winding. This generated signal may be communicated uphole and observed at the surface of the well. Thus, with this technique of detecting casing collar joints, the casing collar locator must be in motion to produce the signal.

The quality of the signal may be highly dependent on the degree to which the magnetic permeability changes, or is disturbed. In this manner, the higher the rate of change in the permeability that is experienced by the magnetic flux field, the higher the induced signal (to a finite degree). The degree to which the field is disturbed depends on such factors as the distance, or gap (also called the "stand-off"), between the casing collar locator and the casing; the magnetic properties (i.e., the permeability) of the surrounding well casing; and the degree of change in geometry or bulk-mass of the casing, i.e., the change must be drastic enough and abrupt enough to cause a rapid enough disturbance in the flux field.

If the field is not sufficiently disturbed, the resulting signal may be too small to be detected at the surface. The signal-to-noise ratio of the signal produced downhole typically places a limit on the degree to which the signal can be boosted, or amplified. Therefore, for these reasons, it may be very difficult to detect joints of casing that is made from a material having a low magnetic permeability, such as Hastalloy, for example. Likewise, collar joints that have no casing collars are difficult to detect, particularly if the joints are "flush" (i.e., each joint has no or almost no air gap).

Another difficulty associated with a conventional casing collar locator is its mass and size. In this manner, the conventional casing collar locator may include two or more permanent magnets, one or more coils, and one or more coil cores, or bobbins. The combination of all of these components imparts a large mass to the casing collar locator. This large mass, in turn, may cause a significant force to be exerted on the casing collar locator during perforating operations due to the high acceleration and shock that is placed on this large mass. This force may damage the casing collar locator if extensive measures are not undertaken to properly pack the casing collar locator in the string.

Besides having a large mass, the casing collar locator typically is quite bulky, as the locator may extend from six to eighteen inches and beyond, not including the pressure housing and connections. The tool string that houses the casing collar locator is therefore long and cumbersome. Tool length is very important particularly when the tool string is conveyed on a wireline and when working with high well pressure. Having a long tool string can present major operational and safety problems with pressure control equipment, such as the lubricator and riser pipe. Therefore, it is typically important to conserve every inch of a tool string, particularly in perforating applications.

Thus, there is a continuing need for an arrangement that addresses one or more of the problems that are stated above.

SUMMARY

In an embodiment of the invention, an apparatus that is usable with a subterranean well includes a magnetometer and a circuit. The magnetometer indicates a strength of a magnetic field that at least partially extends through a portion of a downhole pipe. The circuit is coupled to the magnetometer to indicate a feature present in the pipe based on the indication from the magnetometer.

In another embodiment of the invention, an apparatus that is usable with a subterranean well includes a magnet and a winding. The magnet establishes a flux field near the apparatus, and the flux field at least partially extends through a portion of a downhole pipe. The winding generates a signal produced by a change in a strength of the flux field to indicate a feature of the pipe. The longitudinal dimension of the apparatus does not exceed approximately two inches.

In yet another embodiment of the invention, an apparatus that is usable in a subterranean well includes a first winding, a second winding, a powered interface and an unpowered interface. The first winding generates a first signal in response to a change in a magnetic field that at least partially extends through the first winding and at least partially extends through a portion of a downhole pipe to indicate a feature of the pipe. The second winding generates a second signal in response to a change in the magnetic field to indicate detection of the feature of the pipe. The magnetic field at least partially extends through the second winding. The first interface is coupled to the first winding to communicate the first signal to the surface of the well when the apparatus is in a powered mode, and the second interface is coupled to the second winding to communicate the second signal to the surface of the well when the apparatus is in an unpowered mode.

Additional advantages and other features of the invention will become from the following description, drawing and claims.

DETAILED DESCRIPTION

Figure 1:
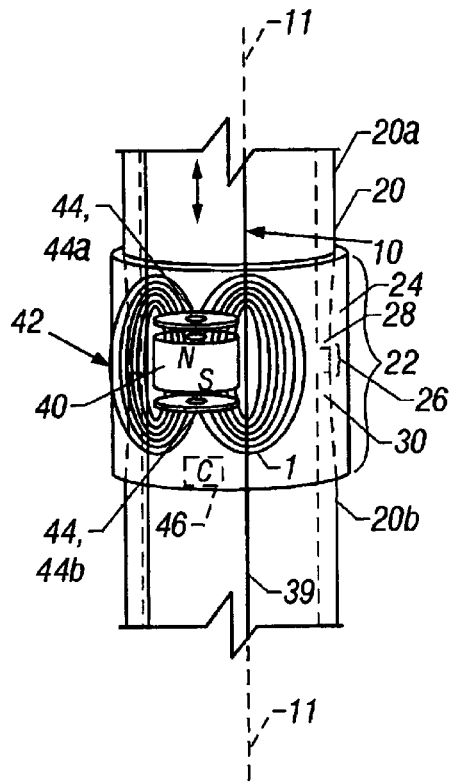
FIGS. 1,3,4 and 6 are schematic diagrams of a magnetic field-based detector according to different embodiments of the invention.

Referring to FIG. 1, an embodiment 10 of a downhole magnetic-field based feature detector in accordance with the invention may be used to locate magnetically distinguishable features of a tubular member, or pipe, that surrounds the feature detector. In this context, the term "pipe" may include a well casing, a valve, a casing collar joint or other tubular structure that has ferromagnetic properties and has a passageway for receiving the feature detector 10. As an example, in some embodiments of the invention, the feature detector 10 may pass through a central passageway of a well casing 20 along a longitudinal axis 11 of the casing 20 for purposes of detecting features of the casing 20, such as a casing collar joint 22. Unlike conventional casing collar detectors, the feature detector 10 does not need to move to generate a signal to indicate a potential feature (a collar joint, for example) of the portion of the pipe near the detector 10. Instead, the feature detector 10 includes one or more magnetometers 44 (an upper magnetometer 44a and a lower magnetometer 44b depicted in FIG. 1, as examples) to sense the strength of a magnetic flux field that is created by a magnet 40 of the detector 10 and extends through a portion of the pipe near the detector 10. Thus, while stationary, the feature detector 10 may be used to detect features of the surrounding pipe.

In this manner, in some embodiments of the invention, the magnetic axis of the magnet 40 is generally parallel to the longitudinal axis 11 of the casing 20 so that flux lines 42 of the magnetic flux field extend between the poles of the magnet 40 in a dipole pattern. The upper magnetometer 44a may be located above the north pole of the magnet 40, and the lower magnetometer 44b may be located below the south pole of the magnet 40, as an example.

As depicted in FIG. 1, some of the flux lines pass through a portion of a wall of the well casing 20, and as a result, the strength of the magnetic field may be controlled by features of the casing 20, as the magnetic field is a function of the effective permeability of the path through which the flux lines 42 pass. Thus, the permeability is affected by the different features of the well casing 20, and as a result, the strength of the magnetic field that is detected by the magnetometers 44 is affected by the different features of the well casing 20. By detecting the strength of the magnetic field, the feature detector 10 may determine when a particular feature (the casing collar joint 22, for example) is in proximity to the detector 10.

For example, the casing collar joint 22 that is depicted in FIG. 1 is formed from the union of two well casing segments 20a and 20b that are coupled together by a casing collar 24. In this manner, a lower tapered end 28 of the upper casing segment 20a extends an upper portion of the collar 24, and an upper tapered end 30 of the lower casing segment 20b extends into the lower portion of the collar 24. The two ends 28 and 30 do not meet inside the collar 24, but rather, an air gap 26 exists between the ends 28 and 30. Thus, the combination of the air gap 26 and the casing collar 24 creates a significantly different permeability for the flux lines 42 of the feature detector 10 when the detector 10 is near the collar joint 22 than the permeability that is present when the feature detector 10 is near a portion of the well casing 20 away from the collar joint 22.

The one or more magnetometers 44 provide an indication of the strength of the magnetic field, and because this strength is different when the feature detector 10 is near the collar joint 22 than when the feature detector 10 is away from the collar joint 22 near a straight section (for example) of the well casing 20, the presence of the collar joint 22 may be detected by comparing the different magnetic field strengths.

The feature detector 10 is to be compared to a conventional casing collar locator that relies on a change in the sensed magnetic field to induce a signal on a winding for purposes of indicating detection of a casing collar joint. Thus, the conventional casing collar locator does not generate a signal if the locator is not moving. In contrast, the feature detector 10 measures a magnetic field strength, regardless of whether the feature detector 10 is moving or not. The difference in field strengths may be used to determine if a casing joint or other feature has been detected.

In general, the changes or disturbances to the established magnetic flux field are caused by such changes as the geometry of the pipe; gaps in the pipe (such as the air gaps present in collar joints); anomalies in the pipe, such as heavy pitting, cracks, or holes such as perforations; sudden changes in distance or stand-offs between the feature detector 10 and the pipe; other changes in the magnetic properties (e.g., permeability) of the pipe; and changes in the bulk-mass of the pipe.

Among the other features of the feature detector 10, in some embodiments of the invention, the detector 10 may include a tubular non-magnetic housing 39 that has a longitudinal axis that is generally aligned with the longitudinal axis 11 of the well casing 20 when the detector 10 is located inside the casing 20. As its name implies, the housing 39 protects and provides sealed containment of the magnetometers 44, the magnet 40 and circuitry 46 of the feature detector 10. As an example, the housing 39 may be connected to a wireline cable 64 (see FIG. 2) that extends to a surface of the well to position the feature detector 10, to communicate signals from the feature detector 10 to the surface and to possibly provide power to the detector 10.

Figure 2:
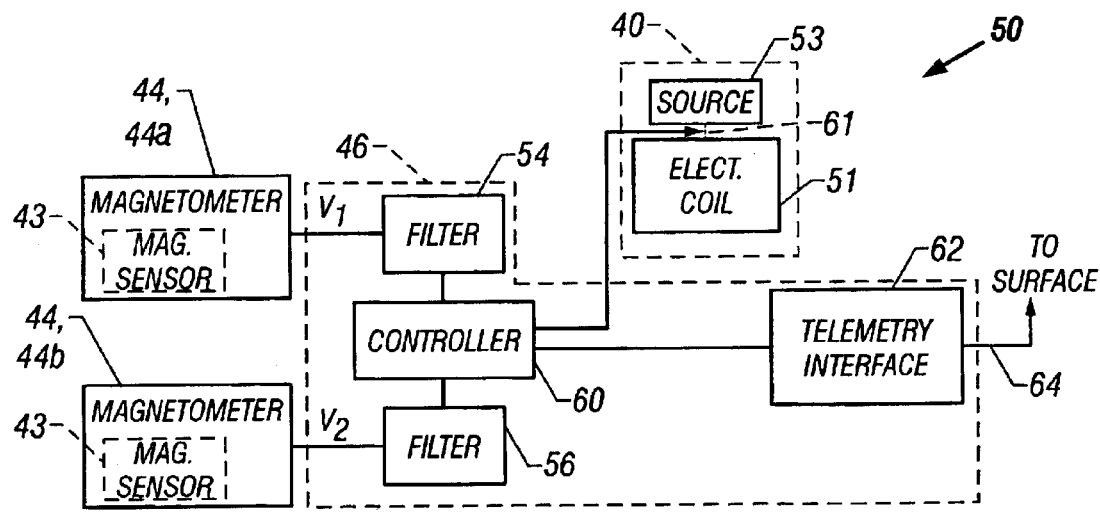
FIG. 2 is a schematic diagram of circuitry of the feature detector of FIG. 1 according to an embodiment of the invention.

Referring also to FIG. 2, in some embodiments of the invention, the circuitry 46 may include a filter 54 that receives a voltage (called V1) from the upper magnetometer 44a and a filter 56 that receives a voltage (called V2) from the lower magnetometer 44b. In this manner, the V1 and V2 voltages indicates the magnetic field strengths sensed by the upper 44a and lower 44b magnetometers, respectively. The filters 54 and 56 may be peak detectors, for example, to detect the peaks of the V1 and V2 voltages for purposes of filtering lower magnitude voltages (i.e., noise) from the V1 and V2 voltages. Other filters (low pass and/or bandpass filters, as examples) may be used.

The output terminals of the filters 46 and 56 provide signals to a controller 60 that determines when a casing joint or other feature of the well casing 20 has been encountered based on the indications from the magnetometers 44a and 44b, in some embodiments of the invention. When a particular feature has been detected, the controller 60 may, in some embodiments of the invention, communicate an indication of the feature to the surface via a telemetry interface 62. As an example, the telemetry interface 62 may establish communication with the wireline cable 64 that extends to the surface of the well. Depending on the particular embodiment of the invention, the controller 60 may communicate to the surface a direct indication of the strength of the magnetic field or alternatively may communicate an indication of an actual feature detected.

The controller 60 may also control the on/off operation of the magnet 40 for embodiments where the magnet 40 is formed from an electrical coil, or winding 51. In this manner, the controller 60 may couple the winding 51 to a signal source 53 (an AC or DC source) via a switch 61 to create the magnetic field. In other embodiments of the invention, the magnet 40 may be a permanent magnet. The size and the position of the magnet 40 relative to the casing 20 may be adjusted to achieve different results, such as sensitivity, radius of investigation, etc.

Each magnetometer 44 includes a magnet sensor 43 that generates a signal indicative of the strength of the sensed magnetic field. As just a few examples, the magnet sensor 43 may be a Hall-effect sensor, a silicon-based sensor (e.g., an anisotropic magnetoresistive (AMR) sensor or a giant magnetoresistive (GMR) sensor), a superconducting quantum interference device (SQUID), a Search-Coil, a magnetic flux gate, or a magnetoinductive device.

As depicted in FIG. 1, in some embodiments of the invention, two or more magnetometers 44 may be used to achieve different modes of detection, such as integration of differential detection (for directional or focused detection, such as movement in only single axis).

Figure 6:
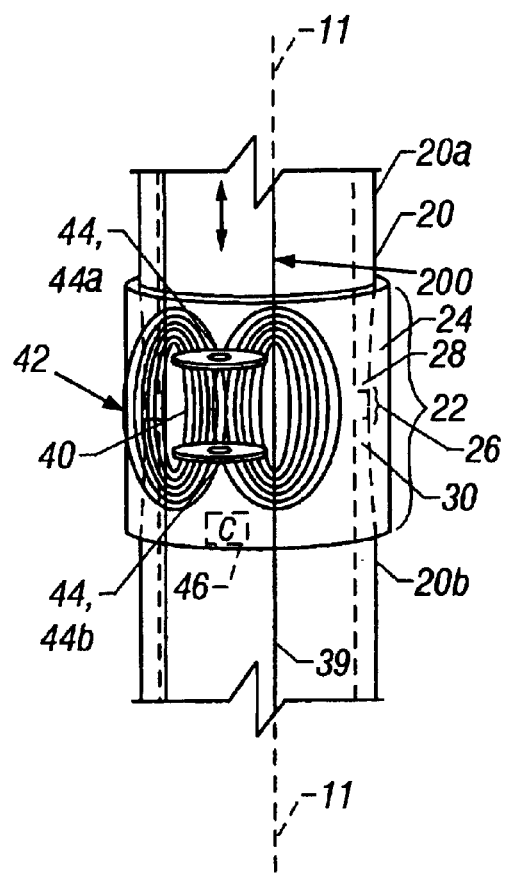

In some embodiments of the invention, the feature detector 10 may not have an explicit magnet source. For these embodiments, the magnetic flux field comes from the "natural magnetism" of the pipe. For example, FIG. 6 depicts an embodiment 200 of a magnetic field-based feature detector that does not include the magnet 40, although the feature detector 200 may otherwise have a design that is similar to the feature detector 10.

The feature detectors (such as the feature detectors 10 and 200 and other feature detectors that are described below) that are described herein may offer one or more of the following advantages over conventional casing collar locators. The feature detector may not (in some embodiments) use an inductance to detect casing collars and thus, may be immune to problems related to detecting a change in inductance. The feature detector may be able to detect changes in pipes that have low magnetic permeability. The feature detector may be able to detect changes from large stand-offs (large air gaps between detector and the surrounding well casing), thus eliminating the need for "outrigger" arms. The feature detector may be sensitive only to changes in the longitudinal axis, thereby eliminating noise that is generated in a conventional casing collar locator when the locator is moved in transverse directions due to vibrations and/or cable movement. The mass and overall size of the feature detector may be greatly reduced, as compared to conventional casing collar locators. Regardless of whether the feature detector is moving, the detector indicates whether the detector is near a casing collar joint. The feature detector may provide precise downhole depth control and measurement that may be used for such applications as double shooting with oriented perforating where the shot spacing is critical; precise setting of orienting packer or whipstocks; and positioning a special cutter or splitter over a critical area of pipe, such as splitting a pipe joint for pipe recovery. Other and different advantages are possible.

Figure 3:
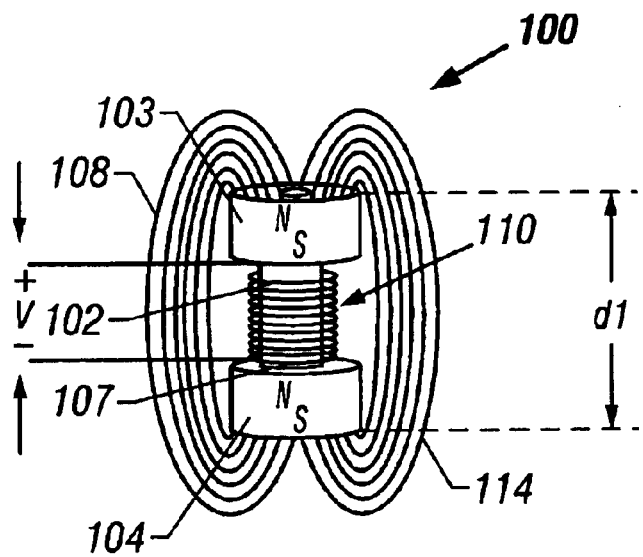

Referring to FIG. 3, in some embodiments of the invention, a feature detector 100 may be used in place of the feature detectors 10 and 70. Unlike conventional feature detectors, the feature detector 100 is constructed with components to minimize the overall size and weight of the detector 100. Due to its low mass, the force that is exerted on the feature detector 100 during perforating operations is significantly less than the force exerted on larger, conventional casing collar locators. As an example, a longitudinal dimension (called $d_1$) of the feature detector 100 may be near two inches or even less.

To achieve its miniature size, the feature detector 100 includes two or more permanent magnets (an upper magnet 103 and a lower magnet 104 depicted as examples) that are each formed from a material (SmCo-30, for example) that has a high magnetic strength. The feature detector 100 also includes a winding 102 that has a high number of turns (40,000 for example) and is located between the permanent magnets 103 and 104 to provide a signal (called V) indicative of the rate at which the flux through the winding 102 changes. The winding 102 may have a high number (approximately 40,000 or more, depending on the particular embodiment) of turns, as compared to the number of turns for a winding used in a conventional casing collar locator. The winding 102 is formed on a bobbin 107 that is formed of a highly permeable magnetic material (Carpenter electrical iron, for example).

In some embodiments of the invention, an apparatus that is usable with a subterranean well includes a magnet to establish a flux field that at least partially extends through a portion of a downhole pipe. The apparatus also includes a winding to generate a signal that is produced by a change in a strength of the flux field to indicate a feature of the pipe. The winding has at least approximately 1000 turns.

Figure 4:
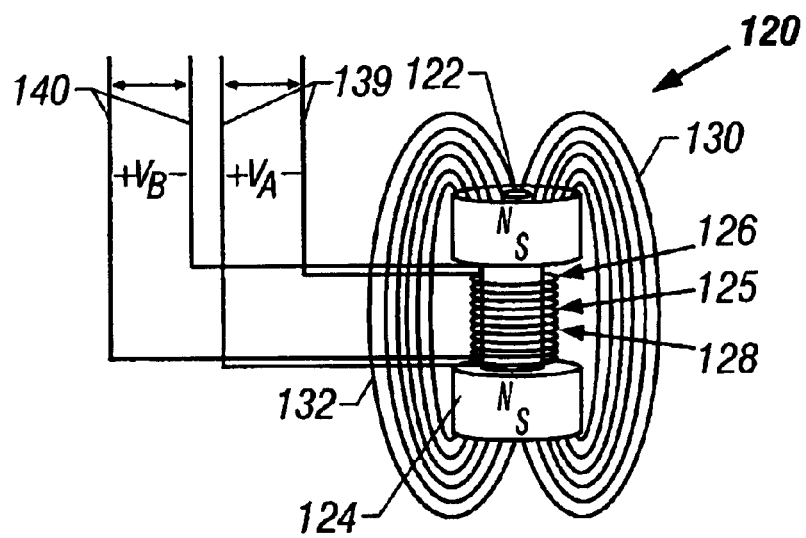

FIG. 4 depicts another embodiment 120 of a magnetic-field based feature detector. The feature detector 120 may or may not have the miniature design of the feature detector 100, depending on the particular embodiment of the invention. The feature detector 120 provides dual modes: a first mode in which the feature detector 120 provides a detection signal without requiring power to be provided to the detector 120 and a second mode in which the feature detector 120 provides a detection signal when the detector 120 receives power. It may be desirable to have an unpowered detector for certain perforating applications. However, in other applications, it may be desirable to power the feature detector 70 for purposes of increasing the strength of the detection signal.

In some embodiments of the invention, the feature detector 120 includes a winding 126 for the powered mode and a winding 128 for the unpowered mode. The windings 126 and 128 may be bi-filar wound on the same bobbin 125 and may be electrically isolated from each other. The feature detector 102 may include an upper permanent magnet 122 and a lower permanent magnet 124 that cooperate to establish a magnetic field, as depicted by the flux lines 130 that extend through along the longitudinal axis of the windings 126 and 128.

The two different windings 126 and 128 are needed for the two different modes due to the signal loss that occurs when a single winding is used for both the powered and unpowered modes. In this manner, with a single winding, the output terminals of the winding drives the signal straight onto the cable when no power is received and drives the signal onto the cable via amplifiers when power is received. Due to this dual use, during the powered mode of operation, the wireline cable may attenuate the signal to the point that the amplifier may not have a sufficient signal.

Figure 5:
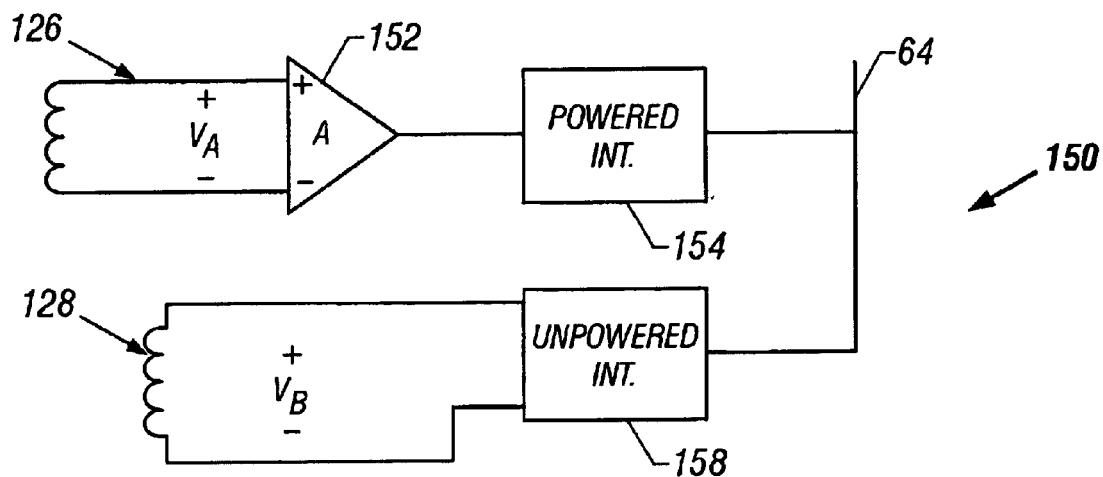
FIG. 5 is a schematic diagram of circuitry of the feature detector of FIG. 4 according to an embodiment of the invention.

Thus, to address this problem, the feature detector 120 includes the two windings 126 and 128 for the different modes and includes different interfaces to drive the signals that are produced by these windings 126 and 128 onto the wireline cable 64. For example, FIG. 5 depicts possible circuitry 150 that may be used. The circuitry 150 includes an instrumentation amplifier 152 that has its input terminals coupled to the terminals 139 of the winding 126 and provides a signal to a powered interface 154 to drive an indication of the signal from the winding 126 onto the cable 64 during the powered mode. The circuitry 150 also includes an unpowered interface 158 (a resistor network, for example) that is coupled to the terminals 140 of the winding 140 to drive an indication of the signal from the winding 128 onto the cable 64 during the unpowered mode.

While the embodiments above are all invented to detect physical (geometrical) changes and changes in magnetic permeability in pipe when the embodiments are conveyed (moved) axially, they are also sensitive to sudden movement in the transverse axis. As such, they can be used for detecting sudden transverse movement of down-hole tools such as explosive devices, for example perforating guns and cutters fire. In one embodiment, the output of any of the above embodiments, can be used to trigger an output signal onto the cable for real-time detection of the detonation event at surface. It may in another embodiment be recorded downhole for post event confirmation of the event for example the detonation.

While the invention has been disclosed with respect to a limited number of embodiments, those skilled in the art, having the benefit of this disclosure, will appreciate numerous modifications and variations therefrom. It is intended that the appended claims cover all such modifications and variations as fall within the true spirit and scope of the invention.

What is claimed is:

1. An apparatus usable with a subterranean well, comprising:
   a magnetometer to indicate a strength of a magnetic field that at least partially extends through a portion of a downhole pipe;
   a circuit coupled to the magnetometer to indicate a feature present in the pipe based on the indication from the magnetometer;
   a magnet to establish the magnetic field; and
   another magnetometer to indicate the strength of the magnetic field downhole,
   wherein the circuit indicates the magnetic feature using the indications from both magnetometers.

2. The apparatus of claim 1, wherein the features comprises at least one of the following:
   a casing collar joint; and a geometry, anomaly, magnetic property or standoff distance associated with the pipe.

3. The apparatus of claim 1, further comprising:
   a telemetry interface to communicate a signal to a surface of the well to indicate the feature.

4. The apparatus of claim 1, wherein the magnetometer comprises a magnetic sensor to detect the strength of the magnetic field.

5. The apparatus of claim 4, wherein the magnetic sensor comprises one of the following:
   a Hall-effect sensor, a silicon-based sensor, a superconducting quantum interference device, a Serach coil, a magnetic flux gaze and a magnetoinductive device.

6. An apparatus usable with a subterranean well, comprising:
   a magnet to establish a flux field near the apparatus, flux field at least partially extending through a portion of a downhole pipe; and
   a winding to generate a signal produced by a change in a strength of the flux field to indicate a feature of the pipe,
   wherein the apparatus has a longitudinal dimension not exceeding approximately two inches.

7. The apparatus of claim 6, wherein the feature comprises at least one of the following:
   a casing collar joint; and a geometry, anomaly, magnetic property or standoff distance associated with the pipe.

8. The apparatus of claim 6, wherein the apparatus has a longitudinal dimension less than or equal to approximately two inches.

9. An apparatus usable in a subterranean well, comprising:
   a first winding to generate a first signal in response to a change in a magnetic field at least partially extending through the first winding and at least partially extending through a portion of a downhole pipe to indicate detection of a feature of the pipe;
   a second winding to generate a second signal in response to a change in the magnetic field to indicate detection of the feature, the magnetic field at least partially extending through the second winding;
   a first interface coupled to the first winding to communicate the first signal to the surface of the well when the apparatus is in a powered mode; and
   a second interface coupled to the second winding to communicate the second signal to the surface of the well when the apparatus in an unpowered mode.

10. The apparatus of claim 9, further comprising:
    a bobbin, wherein the first and second windings are wound around the bobbin.

11. The apparatus of claim 9, wherein the powered interface comprises an amplifier.

12. The apparatus of claim 9, wherein the unpowered interface comprises a resistor network.

13. A method usable in a subterranean well, comprising:
    providing a first winding to generate a first signal in response to a change in a magnetic field at least partially extending through the first winding and at least partially extending through a portion of a downhole pipe to indicate detection of a feature of the pipe;
    providing a second winding to generate a second signal in response to a change in the magnetic field to indicate detection of the downhole feature, the magnetic field at least partially extending through the second winding;
    using a first interface coupled to the first winding to communicate the first signal to the surface of the well in a powered mode; and using a second interface coupled to the second winding to communicate the second signal to the surface of the well in an unpowered mode.

14. The method of claim 13, further comprising:
winding the first and second windings around a bobbin shared in common.

15. The method of claim 13, wherein the first interface comprises an amplifier.

16. The method of claim 13, wherein the second interface comprises a resistor network.

17. A method usable with a subterranean well, comprising:
sensing a strength of a magnetic field that at least partially extends through a portion of a downhole pipe; and
based on the sensed strength, generating a signal indicative of sudden transverse movement.

18. The method of claim 17, wherein the signal indicates at least one of the following:
a casing collar joint; and a geometry, anomaly, magnetic property or standoff distance associated with the pipe.

19. The method of claim 17, further comprising:
using a magnet to establish the magnetic field.

20. The method of claim 17, further comprising:
not using a magnet to establish the magnetic field.

21. The method of claim 17, wherein the signal comprises a signal communicated to a surface of the well indicating the feature.

22. The apparatus of claim 17, wherein the feature comprises at least one of the following:
a casing collar joint; and a geometry, anomaly, magnetic property or standoff distance associated with the pipe.

23. A method usable with a subterranean well, comprising:
using a magnet to establish a flux field that at least partially extends through a portion of a downhole pipe, the magnet being formed from a material having magnetic properties similar to SmCo-30; and
sensing a change in a strength of the flux field to indicate sudden transverse movement.

24. The method of claim 23, wherein the sensed change indicates at least one of the following:
a casing collar joint; and a geometry, anomaly, magnetic property or standoff distance associated with a tubular member that at least partially surrounds the apparatus.

25. A method usable with a subterranean well, comprising:
establishing a magnetic flux field that at least partially extends through a portion of a downhole pipe; and
using a winding to generate a signal produced by a change in a strength of the flux field to indicate sudden transverse movement, the winding having at least approximately 40,000 turns.

26. The method of claim 25, wherein the signal indicates at least one of the following:
a casing collar joint; and a geometry, anomaly, magnetic property or standoff distance associated with the pipe.

27. A method usable in a subterranean well, comprising:
providing a first winding to generate a first signal in response to a change in a magnetic field at least partially extending through the first winding and at least partially extending through a portion of a downhole pipe to indicate sudden transverse movement;
providing a second winding to generate a second signal in response to a change in the magnetic field to indicate detection of the downhole feature, the magnetic field at least partially extending through the second winding;
using a first interface coupled to the first winding to communicate the first signal to the surface of the well in a powered mode; and
using a second interface coupled to the second winding to communicate the second signal to the surface of the well in an unpowered mode.

28. The method of claim 27, further comprising:
winding the first and second windings around a bobbin shared in common.

29. The method of claim 27, wherein the first interface comprises an amplifier.

30. The method of claim 27, wherein the second interface comprises a resistor network.

31. An apparatus usable with a subterranean well, comprising:
a magnet to establish a flux field near the apparatus, the magnet being formed from a material having magnetic properties similar to SmCo-30 and the flux field at least partially extending through a portion of a downhole pipe; and
a winding to generate a signal produced by a change in a strength of the flux field to indicate detection of a feature of the pipe,
wherein the apparatus has a longitudinal dimension less than or equal to approximately two inches.

32. An apparatus usable with a subterranean well, comprising:
a magnet to establish a flux field near the apparatus, the magnet being formed from a material having magnetic properties similar to SmCo-30 and the flux field at least partially extending through a portion of a downhole pipe;
a winding to generate a signal produced by a change in a strength of the flux field to indicate detection of a feature of the pipe; and
a bobbin around which the winding is wound, the bobbin formed from a material having ferromagnetic properties similar to ferromagnetic properties exhibited to Carpenter Electrical iron.

33. An apparatus usable with a subterranean well, comprising:
a magnet to establish a flux field near the apparatus, the magnet being formed from a material having magnetic properties similar to SmCo-30 and the flux field at least partially extending through a portion of a downhole pipe; and
a winding to generate a signal produced by a change in a strength of the flux field to indicate detection of a feature of the pipe,
wherein the apparatus has a longitudinal dimension less than or equal to approximately two inches.

34. An apparatus usable with a subterranean well, comprising:
a magnet to establish a flux field near the apparatus, the magnet being formed from a material having magnetic properties similar to SmCo-30 and the flux field at least partially extending through a portion of a downhole pipe;
a winding to generate a signal produced by a change in a strength of the flux field to indicate detection of a feature of the pipe; and a bobbin around which the winding is wound, the bobbin formed from a material having ferromagnetic properties similar to ferromagnetic properties exhibited to Carpenter Electrical iron.

35. An apparatus usable with a subterranean well, comprising:

a magnet to establish a flux field that extends at least partially through a portion of a downhole pipe; and a winding to generate a signal produced by a change in a strength of the flux field to indicate detection of a feature of the pipe, the winding having at least approximately 40,000 turns, wherein the apparatus has a longitudinal dimension less than or equal to approximately two inches.

* * * * *